US006936751B2

(12) United States Patent  
Charne et al.

(10) Patent No.: US 6,936,751 B2  
(45) Date of Patent: Aug. 30, 2005

(54) BRASSICA WITH EARLY MATURITY RESISTANCE TO AN AHAS-INHIBITOR HERBICIDE AND BLACKLEG DISEASE

(75) Inventors: David G. Charne, Guelph (CA); Jayantilal D. Patel, Thornhill (CA); Gregory R. Gingera, Saskatoon (CA)

(73) Assignee: Pioneer Hi-Bred International, Inc., Johnston, IA (US)

( * ) Notice: Subject to any disclaimer, the term of this patent is extended or adjusted under 35 U.S.C. 154(b) by 129 days.

(21) Appl. No.: 09/993,751

(22) Filed: Nov. 16, 2001

(65) Prior Publication Data

US 2002/0138881 A1 Sep. 26, 2002

(30) Foreign Application Priority Data

Nov. 17, 2000 (CA) .............................. 2326285

(51) Int. Cl.$^7$ ............................. A01H 1/00; A01H 4/00; A01H 5/00; A01H 5/10
(52) U.S. Cl. ...................... 800/306; 435/418; 800/260; 800/266; 800/298; 800/300
(58) Field of Search ................................ 435/418, 430; 800/266, 269, 265, 300, 306, 301

(56) References Cited

U.S. PATENT DOCUMENTS

| | | | | |
|---|---|---|---|---|
| 5,387,758 A | | 2/1995 | Wong et al. ................ | 800/264 |
| 5,545,821 A | | 8/1996 | Wong et al. ................ | 800/300 |
| 5,767,366 A | | 6/1998 | Sathasivan et al. ......... | 800/300 |
| 5,773,702 A | | 6/1998 | Penner et al. .............. | 800/268 |
| 5,850,009 A | * | 12/1998 | Kevern ...................... | 800/271 |
| 6,288,307 B1 | * | 9/2001 | Patel ......................... | 800/306 |
| 6,303,849 B1 | | 10/2001 | Potts et al. ................ | 800/306 |

OTHER PUBLICATIONS

Pang et al 1996, Theor. Appl. Genet. 92:382–387.*
Harker et al, Canadian Journal of Plant Science, Jul. 2000, 80(3):647–654.*
Miki, et al., 1990, *Theoretical and Applied Genetics*, 80:449–458, "Transformation of *Brassica napus* canola cultivars with *Arabidopsis thaliana* acetohydroxyacid synthase genes and analysis of herbicide resistance".
Swanson, et al., 1988, *Plant Cell Reports*, 7:83–87, "The characterization of herbicide tolerant plants in *Brassica napus* L. after in vitro selection of microspores and protoplasts".
Rutledge, et al., 1991, *Mol. Gen. Genet.*, 229:31–40, "Molecular characterization and genetic origin of the *Brassica napus* acetohydroxyacid synthase multigene family".
Ouellet, et al., 1992, *Plant Journal*, 2:321–330, "Members of the acetohydroxyacid synthase multigene family of *Brassica napus*, have divergent patterns of expression".
Hattori, et al., 1992, *Can J. Bot.*, 70: 1957–1963, "DNA sequence relationships and origins of acetohydroxy acid synthase genes of *Brassica napus*".
Swanson, et al., 1989, *Theor. Appl. Genet.*, 78:525–530, "Microspore mutagenesis and selection: Canola plants with field tolerance to imidazolinones".
Newhouse, et al., 1992, *Plant Physiol.*, 100:882–886, "Tolerance to imidazolinone herbicides in wheat".
Sprague, et al., 1997, *Weed Technology*, 11:241–247, "Common cocklebur (*Xanthium strumarium*) resistance to selected ALS–inhibiting herbicides".
Wright, et al., 1998, *Weed Science*, 46:24–29, "In vitro and whole–plant magnitude and cross–resistance characterization of two imidazolinone–resistant sugarbeet (*Beta vulgaris*) somatic cell selections".
Seefeldt, et al., 1998, *Weed Science*, 46:632–634, "Production of herbicide–resistant jointed goatgrass (*Aegilops cylindrica*) x wheat (*Triticum aestivum*) hybrids in the field by natural hybridization".
Harms, et al., 1992, *Mol. Gen. Genet.*, 233:427–435, "Herbicide resistance due to amplification of a mutant acetohydroxyacid synthase gene".
Lee, et al., 1988, *The Embro Journal*, 7:1241–1248, "The molecular basis of sulfonylurea herbicide resistance in tobacco".
Lovell, et al., 1996, *Weed Science*, 44:789–794, "Imidazolinone and sulfonylurea resistance in a biotype of common waterhemp (*Amaranthus rudis*)".
Foes, et al., 1999, *Weed Science*, 47:20–27, "A kochia (*Kochia scoparia*) biotype resistant to triazine and ALS–inhibiting herbicides".
Bing, D., 1991, M. Sc. Thesis, University of Saskatchewan, "Potential of gene transfer among oilseed brassica and their weedy relatives".
Newhouse, et al., 1988, *American Chemical Society Symposium Series Managing Resistance to Agrochemicals*, 421:474–482, "Genetic Modification of Crop Responses to Imidazolinnone Herbicides".
Fehr, W.R., et al., 1987, *Mutation Breeding*, 1:286–303, "Principles of Cultivar Development".
Hattori, J., et al., 1995, *Mol Gen Genet*, 246: 419–425, "An Acetohydroxy acid synthase mutant reveals a single site involved in multiple herbicide resistance".
Hobbs, S.L.A., 1987, *Can. J. Plant Sci.*, 67: 457–466, "Comparison of Photosynthesis in Normal and Triazine–Resistant".
Chevre et al., Selection of stable *Brassica napus–B. juncea* recombinant lines resistant to blackleg (*Leptosphaeria maculans*). 1. Identification of molecular markers, chromosomal and genomic origin of the introgression, Theor. Appl. Genet. (1997) 95:1104–1111.

(Continued)

Primary Examiner—David H Kruse
(74) Attorney, Agent, or Firm—Pioneer Hi-Bred International, Inc.

(57) ABSTRACT

Improved varieties of Brassica having an "R" rating for blackleg and resistance to AHAS-inhibitor herbicides, are provided. These varieties may be used to produce inbreds or hybrids or to produce vegetable oil and meal. Parts of these plants, including plant cells, are also provided

18 Claims, No Drawings

OTHER PUBLICATIONS

Barret et al., Selection of stable *Brassica napus–Brassica juncea* recombinant lines resistant to blackleg (*Leptosphaeria maculans*). 2. A 'to and fro' strategy to localise and characterise interspecific introgressions of the *B. napus* genome, Theor. Appl. Genet. (1998) 96:1097–1103.

Prakash et al., Introgression of Resistance to Shattering in *Brassica napus* from *Brassica juncea* through Non–Homologous Rcombination, Plant Breeding (1988) 101:167–168.

Struss et al., Mapping of Molecular Markers on Brassica B–Genome Chromosomes Added to *Brassica napus* (1992) 108:320–323.

* cited by examiner

BRASSICA WITH EARLY MATURITY RESISTANCE TO AN AHAS-INHIBITOR HERBICIDE AND BLACKLEG DISEASE

FIELD OF THE INVENTION

This invention is in the field of canola breeding. In particular, it relates to improved varieties of *Brassica* having an "R" rating for blackleg and resistance to at least one AHAS-inhibitor herbicide.

CROSS-REFERENCE TO RELATED APPLICATIONS

This application claims priority under 35 USC 119(a) to Canadian Application No. 2,326,285 filed Nov. 17, 2001 the disclosure of which is incorporated herein by reference.

BACKGROUND OF THE INVENTION

Canola is an important agricultural crop in Canada, the United States, Europe and Australia. Weed competition and blackleg disease are significant limiting factors in canola crop production and quality. The challenge for plant scientists has been to develop canola varieties having superior performance with respect to these limiting factors, while at the same time having satisfactory agronomic characteristics, including yield potential, lodging resistance, oil and protein content, and glucosinolate levels that are sufficiently low for registration.

RESISTANCE TO AHAS-INHIBITOR HERBICIDES

Herbicide resistant plants are plants that are able to survive and reproduce following exposure to herbicides at rates of application that would prevent non-herbicide resistant varieties of the same species from surviving and reproducing. Herbicide resistance is particularly important for *Brassica,* since many weeds, such as stinkweed, shepherd's purse, flixweed, ball mustard, wormseed mustard, hare's ear mustard and common peppergrass have a close genetic relationship with *Brassica* species. Therefore, it is advantageous for a cultivar to have herbicide resistance not possessed by related weeds.

Some herbicides function by disrupting amino acid biosynthesis in affected species. For example, AHAS-inhibitor herbicides, (also known as ALS-inhibitor herbicides), function by inhibiting the enzyme acetohydroxy acid synthase (AHAS), the first enzyme in the biosynthesis of the amino acids, isoleucine, leucine, and valine. In plants with resistance to an AHAS-inhibitor herbicide, inhibition of the AHAS enzyme is prevented, thus allowing the plant to continue with normal amino acid biosynthesis. Most forms of *Brassica* are highly susceptible to AHAS-inhibitor herbicides, such as imidazolinones and sulfonylureas.

The development of canola with resistance to imidazolinones, such as PURSUIT™ and ODYSSEY™, was a major breakthrough in weed management technology. The imidazolinones are a family of broad spectrum herbicides which may be applied for in-crop weed control. They control a larger number of problem species than herbicides used in non-herbicide resistant varieties, and offer greater management flexibility, including timing of application and tank mixing. An advantage of imidazolinone ("IMI") resistant varieties over other herbicide resistant varieties, such as ROUNDUP READY™ (glyphosate) or LIBERTY LINK™ (glufosinate) resistant varieties, is that some imidazolinone herbicides have a soil residual which controls successive weed flushes. This provides a significant advantage to farmers, because it enables them to achieve longer term weed control without a second application of herbicide. Effective weed control increases yield by reducing competition from weed species. It also improves grain quality through the elimination of cruciferous weed seeds. It may also improve weed management in other crops in the rotation, due to reduced weed pressure.

However, a drawback of currently available IMI resistant varieties is that they lack many of the desirable traits found in elite varieties of non-herbicide resistant canola. In particular, none of the currently available IMI resistant varieties have a resistant ("R") rating to blackleg disease. It is particularly difficult to develop varieties having IMI resistance in combination with other desirable traits because the inheritance of the IMI resistance trait is relatively complex. Unlike the ROUNDUP READY™ trait or LIBERTY LINK™ trait, which are controlled by single transgenes that exhibit complete dominance, the IMI resistance trait is controlled by two unlinked gene pairs having partial dominance. Swanson et al., Plant Cell Reports 7:83–87 (1989) reported the development of imidazolinone herbicide tolerant *Brassica napus* mutants using microspore mutagenesis. During the process, five fertile double-haploid *Brassica napus* mutant plants were developed. One of the mutants was tolerant to between 5 and 10 times the recommended field traits of an imidazolinone herbicide. An inheritance study indicated that two semi-dominant unlinked genes combined to produce an F1 with greater tolerance than either of the parents.

Rutledge et al., Mol. Gen. Genet. 229:31–40 (1991) proposed a model for the inheritance of the five AHAS genes in *Brassica napus*. AHAS2, AHAS3 and AHAS4 appear to be associated with the 'A' (*rapa*) genome and AHAS1 and AHAS5 are likely associated with the 'C' (*oleracea*) genome. AHAS1 and AHAS3 are expressed at all growth stages (Ouellet et al., Plant J. 2:321–330 1992) and mutant forms of AHAS1 and AHAS3 appear to be the most effective tolerance genes. AHAS2 was found to be active only in ovules and seeds. AHAS4 was found to be defective due to interrupted sequences in the middle of the coding region (Rutledge et al., Mol. Gen Genet. 229:31–40 1991) and was not expressed in tissues examined by Ouellet et al., Plant J. 2:321–330 (1992). The last gene, AHAS5, may also be defective (Rutledge et al. Mol. Gen Genet. 229:31–40, 1991). Hattori et al., Can J. Bot: 70:1957-1963, (1992) determined that the DNA sequence of the coding regions for AHAS1 and AHAS3 were 98% identical. DNA sequences of the 5' and the 3' ends were also closely related. Few similarities were observed between the sequences of the AHAS2 compared to the AHAS1 or AHAS3 genes.

Thus, there are two known effective mutations for AHAS-inhibitor herbicide resistance—an AHAS1 mutant (believed to be located on the C genome) and an AHAS3 mutant (believed to be located on the A genome). The AHAS3 mutant provides resistance to other AHAS-inhibitor herbicides, such as sulfonylureas. *B. napus, B. juncea,* and *B. rapa* all contain the A genome, however only *B. napus* naturally contains the C genome. The AHAS3 resistance gene alone provides protection under moderate herbicide application rates. Under high herbicide application rates, the AHAS3 mutant shows some injury and delay in maturity. The AHAS1 mutant alone, by contrast, shows severe stunting and is very late to flower and mature at even moderate herbicide application rates. Accordingly, both AHAS1 and AHAS3 mutant genes appear to be required for full resistance. The complexity of the inheritance of the IMI resistant trait results in multiple phenotypes during segregating generations, which presents a significant hurdle to plant breeders. Accordingly, there is a need to develop AHAS-inhibitor herbicide resistant varieties having improved performance characteristics.

BLACKLEG RESISTANCE

Blackleg, caused by the fungus *Phoma lingam* (*Leptosphaeria maculans*), is considered the most serious disease of canola worldwide. The fungus causes lesions on the cotyledons, stems, pods, and leaves of canola plants. Stem cankers formed early in the season may girdle the stem, causing lodging and plant death. Less severely affected plants may remain standing but have restricted moisture and nutrient flow, causing the plant to ripen prematurely with shriveled seeds and pods. Infection of canola pods may cause the pods to shatter prior to harvest, resulting in seed loss. Pod infection also results in infection of the seed, which may lead to loss of seed viability. Blackleg is therefore a serious threat to canola yield. Accordingly, plant scientists have invested years of research in attempting to develop canola varieties with superior levels of resistance to blackleg infection.

The Western Canadian Canola/Rapeseed Recommending Committee (WCC/RRC) is a government mandated organization that evaluates canola varieties in Canada and recommends varieties that meet certain criteria for registration by the Canadian Food Inspection Agency. The WCC/RRC uses a classification system to indicate the degree of resistance of canola varieties to blackleg infection. Varieties being tested are compared to the susceptible check variety, Westar, in an inoculated, approved disease screening trial. Testing procedures are set out in a document entitled "Procedures of the Western Canada Canola/Rapeseed Recommending Committee Incorporated for the Evaluation and Recommendation for Registration of Canola/Rapeseed Candidate Cultivars in Western Canada" which is available from the Canola Council of Canada. Canola varieties are placed in one of the following categories, based on a comparison of their disease score with the Westar check variety disease score, as set out below:

| Disease Score* | Rating Classification |
|---|---|
| >90 | Highly susceptible |
| 70 to 90 | Susceptible |
| 50 to 70 | Moderately susceptible |
| 30 to 50 | Moderately resistant |
| <30 | Resistant ("R") |

*Expressed as a percentage of the Westar check variety disease score.

Canola varieties with a resistant ("R") rating are considered highly desirable by farmers, due to the decreased risk of damage from blackleg disease. Canola varieties having an "R" rating for blackleg, combined with resistance to an AHAS-inhibitor herbicide such as an imidazolinone, would be particularly desirable. This trait combination would provide improved weed control, while increasing or stabilizing yield by reducing risk of crop loss due to blackleg disease. There are no known canola varieties that provide this advantageous combination of traits. Accordingly, it is an object of the present invention to provide an improved variety of *Brassica* having an "R" rating for blackleg and resistance to at least one AHAS-inhibitor herbicide.

SUMMARY OF THE INVENTION

This invention provides a *Brassica* plant having an "R" rating for blackleg and resistance to at least one AHAS-inhibitor herbicide, such as an imidazolinone (e.g. imazethapyr or imazamox) or a sulfonylurea [e.g. thifensulfuron methyl (REFINE™)]. In one embodiment, the plant is a *Brassica napus* plant, such as canola variety 46A76 or NS3213. In another embodiment, the plant is a *Brassica rapa* plant or a *Brassica juncea* plant.

This invention also relates to tissue cultures of regenerable cells from the plants described above, as well as to the use of the tissue cultures for regenerating *Brassica* plants having an "R" rating for blackleg and resistance to at least one AHAS-inhibitor herbicide, such as an imidazolinone or a sulfonylurea. It further relates to the plants regenerated from the tissue culture.

This invention also relates to parts of the *Brassica* plants described above, including their cells, pollen, ovules, roots, leaves, seeds, microspores and vegetative parts, whether mature or embryonic. It further relates to the use of these plant parts for regenerating a *Brassica* plant that has an "R" rating for blackleg and resistance to at least one AHAS-inhibitor herbicide, such as an imidazolinone or a sulfonylurea. It further relates to the plants regenerated from the plant parts.

This invention further relates to the use of the plants described above for breeding a *Brassica* line, through pedigree breeding, crossing, self-pollination, haploidy, single seed descent (SSD), modified single seed descent, backcrossing, or other suitable breeding methods, and to the plants produced therefrom.

This invention also relates to a method for producing a first generation (F1) hybrid *Brassica* seed by crossing one of the plants described above with an inbred *Brassica* plant of a different variety or species and harvesting the resultant first generation (F1) hybrid *Brassica* seed. It further relates to the hybrid plants produced from the F1 hybrid *Brassica* seed and the parts of those plants.

This invention also relates to the use of a *Brassica* plant having an "R" rating for blackleg and resistance to at least one AHAS-inhibitor herbicide, such as canola variety 46A76 or NS3213, for preparing oil and/or meal, and to the vegetable oil and meal produced therefrom. Preferably the oil has less than 2% erucic acid and the meal has less than 30 micromoles of glucosinolates per gram of defatted meal.

This invention provides substantial value to both producers and users of canola by providing hitherto unavailable combinations of an "R" rating for blackleg and resistance to at least one AHAS-inhibitor herbicide. This trait combination improves weed control, while increasing or stabilizing yield by reducing risk of crop loss due to blackleg disease.

DETAILED DESCRIPTION OF THE INVENTION

In accordance with this invention, improved varieties of *Brassica* having an "R" rating for blackleg and resistance to at least one AHAS-inhibitor herbicide are developed by crossing a parent that is resistant to at least one AHAS-inhibitor herbicide, with one or more parents having an "R" rating to blackleg, wherein the herbicide resistant parent and the blackleg resistant parent(s) together have the genetic basis for the complement of characteristics desired in the progeny. Self-pollination or sib-mating following crossing leads to a segregation of traits among the progeny. Progeny having the desired combination of traits are selected after controlled exposure to blackleg disease and one or more appropriate AHAS-inhibitor herbicides and evaluation for other desirable traits over successive generations. Various breeding methods may be used, including haploidy, pedigree breeding, single-seed descent, modified single seed descent, recurrent selection, and backcrossing.

B. napus

Because of the complex inheritance of resistance to AHAS-inhibitor herbicides, we have found that haploidy is the most effective breeding method for B. napus species. Parents having the genetic basis for the desired complement of characteristics are crossed in a simple or complex cross. Crossing (or cross-pollination) refers to the transfer of pollen from one plant to a different plant. Progeny of the cross are grown and microspores (immature pollen grains) are separated and filtered, using techniques known to those skilled in the art [(e.g. Swanson, E. B. et al., "Efficient isolation of microspores and the production of microspore-derived embryos in Brassica napus, L. Plant Cell Reports, 6: 94–97 (1987); and Swanson, E. B., Microspore culture in Brassica, pp. 159–169 in Methods in Molecular Biology, vol. 6, Plant Cell and Tissue Culture, Humana Press, (1990)]. These microspores exhibit segregation of genes. The microspores are cultured in the presence of an appropriate AHAS-inhibitor herbicide, such as imazethapyr (e.g. PURSUIT™) or imazamox (e.g. RAPTOR™) or a 50/50 mix of imazethapyr and imazamox (e.g. ODYSSEY™), which kills microspores lacking the mutations responsible for resistance to the herbicide. Microspores carrying the genes responsible for resistance to the herbicide survive and produce embryos, which form haploid plants. Their chromosomes are then doubled to produce doubled haploids.

The doubled haploids are evaluated in subsequent generations for herbicide resistance, blackleg resistance, and other desirable traits. Resistance to AHAS-inhibitor herbicides may be evaluated by exposing plants to one or more appropriate AHAS-inhibitor herbicides and evaluating herbicide injury. Blackleg resistance may be evaluated by inoculating plants with blackleg spores to induce the disease, and observing resistance to the infection. Some traits, such as lodging resistance and plant height, may be evaluated through visual inspection of the plants, while earliness of maturity may be evaluated by a visual inspection of seeds within pods (siliques). Other traits, such as oil percentage, protein percentage, and total glucosinolates of the seeds may be evaluated using techniques such as Near Infrared Spectroscopy.

It is also possible to analyze the genotype of the plants, using techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as "Microsatellites".

Evaluation and manipulation (through exposure to one or more appropriate AHAS-inhibitor herbicides and blackleg infection) typically occurs over several generations. The performance of the new lines is evaluated using objective criteria in comparison to check varieties. Lines showing the desired combinations of traits are self-pollinated to produce seed. Self-pollination refers to the transfer of pollen from one flower to the same flower or another flower of the same plant. Plants that have been self-pollinated and selected for type for many generations become homozygous at almost all gene loci and produce a uniform population of true breeding progeny.

Other breeding methods may also be used. For example, pedigree breeding is commonly used for the improvement of largely self-pollinating crops such as canola. Pedigree breeding starts with the crossing of two genotypes, each of which may have one or more desirable characteristics that is lacking in the other or which complements the other. If the two original parents do not provide all of the desired characteristics, additional parents can be included in the crossing plan.

These parents are crossed in a simple or complex manner to produce a simple or complex $F_1$. An $F_2$ population is produced from the F1 by selfing one or several $F_1$ plants, or by intercrossing two $F_1$'s (i.e., sib mating). Selection of the best individuals may begin in the $F_2$ generation, and beginning in the $F_3$ the best families, and the best individuals within the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines commonly are tested for potential release as new cultivars. However, the pedigree method is more time-consuming than the haploidy method for developing improved IMI resistant plants, because the plants exhibit segregation for multiple generations, and the recovery of desirable traits is relatively low.

The single seed descent (SSD) procedure may also be used to breed improved varieties. The SSD procedure in the strict sense refers to planting a segregating population, harvesting a sample of one seed per plant, and using the population of single seeds to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the plants originally sampled in the F2 population will be represented by a progeny when generation advance is completed.

In a multiple-seed procedure, canola breeders commonly harvest one or more pods from each plant in a population and thresh them together to form a bulk. Part of the bulk is used to plant the next generation and part is put in reserve. The procedure has been referred to as modified single-seed descent or the pod-bulk technique. The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Backcross breeding can be used to transfer a gene or genes for a simply inherited, highly heritable trait from a source variety or line (the donor parent) into another desirable cultivar or inbred line (the recurrent parent). After the initial cross, individuals possessing the phenotype of the donor parent are selected and are repeatedly crossed (backcrossed) to the recurrent parent. When backcrossing is complete, the resulting plant is expected to have the attributes of the recurrent parent and the desirable trait transferred from the donor parent.

Improved varieties may also be developed through recurrent selection. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

B. juncea

Similar methods may be used to develop B. juncea varieties having an "R" rating for blackleg and resistance to at least one AHAS-inhibitor herbicide. For example, an R-rated mustard quality variety of B. juncea such as DOMO™ 0r CUTLASS™, available from Agriculture and Agri-Food Canada, could be crossed with an IMI resistant canola quality variety of B. juncea such as 98SJ-23841, 98SJ-23844, or 98SJ-23845, seed of which has been deposited by Pioneer Hi-Bred International, Inc. at the American Type Culture Collection (ATCC), Manassas, Va. 20852, and assigned ATCC Accession Nos. PTA-1406, PTA-1407, and PTA-1408 respectively. As used herein, "canola quality" refers to Brassica varieties having oil that contains less than 2% erucic acid and meal that contains less than 30 micromoles of any one or any mixture of 3-butenyl glucosinolate, 4-pentenyl glucosinolate, 2-hydroxy-3 butenyl glucosinolate, and 2-hydroxy-4-pentenyl glucosinolate per gram of air-dry, oil free solid, in accordance with the standards set by the Canola Council of Canada. In comparison, mustard quality canola has higher levels of glucosinolates.

Progeny of the F1 generation would be selected and propagated over successive generations using any of the breeding methods described above. Preferably, the F1 generation is selfed and the F2 generation is propagated through pedigree breeding. Alternatively, the F1 plants could be crossed back to the IMI resistant parent, and the F2 generation could be propagated using pedigree breeding or other breeding methods described above. The progeny would be manipulated and selected over successive generations, through inoculation with blackleg spores, exposure to one or more appropriate AHAS-inhibitor herbicides, and selection for other desirable qualities, according to the methods described herein and known to those skilled in the art.

B. rapa

Similar methods may be used to develop B. rapa varieties having an "R" rating for blackleg and resistance to at least one AHAS-inhibitor herbicide. For example, commercially available B. rapa, such as REWARD™, GOLDRUSH™, or KLONDIKE™ could be crossed with an "R" rated B. napus species, such as canola variety 46A65, which is commercially available from Pioneer Hi-Bred Production Ltd. The F1 could then be crossed with an IMI resistant B. napus variety, and the F2 backcrossed with the original B. rapa variety. Interspecific crosses are used to introduce the desirable IMI resistant and "R" for blackleg traits into a B. rapa variety. One or more backcrosses to B. rapa varieties may be necessary to ensure that the progeny retains the B. rapa phenotype. One would then screen for IMI resistance and an "R" rating for blackleg over successive generations, using the methods described herein. Various breeding methods could be used, as described herein, with the exception that self-pollination is difficult in B. rapa.

Alternatively, one could cross a commercially available B. rapa, such as REWARD™, GOLDRUSH™, or KLONDIKE™, with an IMI resistant B. napus variety that has an "R" rating for blackleg, such as canola variety 46A76, disclosed herein. The F1 progeny could be backcrossed with the B. rapa parent for one or more generations to ensure that the progeny retain the B. rapa phenotype. The resultant progeny could then be manipulated, selected and bred, using the methods described herein.

Regeneration of Plants

This invention also relates to the parts of the plants disclosed herein, including plant cells, tissue, pollen, ovules, roots, leaves, seeds, and microspores, whether mature or embryonic.

The plants produced in accordance with the present invention may be regenerated from plant parts using known techniques. For instance, seeds from the plants of the present invention may be planted in accordance with conventional Brassica growing procedures. These plants will generate further seeds following self-pollination. Alternatively, doubled haploid plantlets may be extracted to immediately form homozygous plants, using known procedures.

Brassica plants may also be regenerated using tissue culture and regeneration. Tissue culture of various tissues of canola and regeneration of plants therefrom is known to those skilled in the art. For example, the propagation of a canola cultivar by tissue culture is described in the following references: Chuong et al., "A Simple Culture Method for Brassica Hypocotyl Protoplasts", Plant Cell Reports 4:4–6 (1985); Barsby, T. L. et al. "A Rapid and Efficient Alternative Procedure for the Regeneration of Plants from Hypocotyls Protoplasts of Brassica napus", Plant Cell Reports, (Spring 1996); Kartha, K. et al. "In vitro Plant Formation from Stem Explants of Rape" Physiol. Plant, 31:217–220 (1974); Narashimhulu, S. et al., "Species Specific Shoot Regeneration Response of Cotyledenary Explants of Brassicas", Plant Cell Reports, (Spring 1988); Swanson, E., "Microspore Culture in Brassica", Methods of Molecular Biology, Vol. 6, Chapter 17, p. 159 (1990).

Use of Brassica as a Breeding Line

The Brassica plant of this invention may be used to breed a novel Brassica line. The combination of desired traits described herein, once established, can be transferred into other Brassica plants of the same species by known plant breeding techniques including self-pollination, crossing, recurrent selection, backcross breeding, pedigree breeding, single seed descent, modified single seed descent, haploidy, and other suitable breeding methods.

The desired traits can also be transferred between Brassica species, such as B. napus, B. rapa, and B. juncea, using the same known plant breeding techniques involving pollen transfer and selection. The transfer of traits between Brassica species, such as napus and rapa by known plant breeding techniques is well documented in the technical literature (see for instance, Tsunada et al., 1980, Brassica Crops and Wild Alleles Biology and Breeding", Japan Scientific Press, Tokyo).

As an example of the transfer of the desired traits described herein from napus to rapa, one selects a commercially available rapa variety such as REWARD™, GOLDRUSH™, and KLONDIKE™, and carries out an interspecific cross with one of the plants from the present invention. After the interspecific cross, members of the F1 generation are self-pollinated to produce $F_2$ oilseed. Selection for the desired traits is then conducted on single $F_2$ plants which are then backcrossed with the *rapa* parent through the number of generations required to obtain a euploid (n=10) *rapa* line exhibiting the desired combination of traits.

In order to avoid inbreeding depression (e.g. loss of vigor and fertility) that may accompany the inbreeding of *Brassica rapa*, selected, i.e. $BC_1$ plants that exhibit similar desired traits while under genetic control advantageously can be sib-mated. The resulting oilseed from these crosses can be designated $BC_1SIB_1$ oilseed. Accordingly, the fixation of the desired alleles can be achieved in a manner analogous to self-pollination while simultaneously minimizing the fixation of other alleles that potentially exhibit a negative influence on vigor and fertility.

This invention is also directed to methods for producing an F1 hybrid seed and plant by crossing a first parent *Brassica* plant with a second parent *Brassica* plant, wherein either the first or second *Brassica* plant is an inbred *Brassica* plant, such as canola variety 46A76 or NS3213, having an "R" rating for blackleg and resistance to at least one AHAS-inhibitor herbicide. This invention is also directed to the plant cells and other parts of the plants produced by these crosses.

Alternatively, both first and second parent *Brassica* plants can come from one of these new varieties. Advantageously, one of the *Brassica* varieties of the present invention is crossed with a different *Brassica* inbred variety, of the same species or a different species, to produce first generation ($F_1$) canola hybrid seeds and plants with superior characteristics and increased vigor.

Preferably when generating hybrid plants, the other parent should have a glucosinolate level that is sufficiently low to ensure that the seed of the $F_1$ hybrid has glucosinolate levels within regulatory limits. The glucosinolate level of the seed harvested from the $F_1$ hybrid is roughly the average of the glucosinolate levels of the male and female parents. For example, if the objective is to obtain hybrid grain ($F_2$) having a glucosinolate level of less than 20 µmol/g, and one parent has a glucosinolate level of 15 µmol/g, the other parent must have a glucosinolate level of 25 µmol/g or less.

Vegetable Oil and Meal

The seed of the plants of this invention may be used for producing vegetable oil and meal, using techniques known to those skilled in the art. The seed of these varieties, the plant produced from such seed, the hybrid canola plant produced from the crossing of these varieties with other inbred varieties, the resulting hybrid seed, and various parts of the hybrid canola plant can be utilized in the production of an edible vegetable oil or other food products in accordance with known techniques. The remaining solid meal component derived from seeds can be used as a nutritious livestock feed. Preferably, the oil has less than 2% erucic acid and the meal has less than 30 micromoles of glucosinolates per gram of defatted meal.

EXAMPLES

The preferred embodiments of this invention are set forth below. It should be understood, however, that the invention is not limited to the specific details set forth in the examples.

Example 1

Development of the Improved IMI Resistant *Brassica napus* Line, 46A76.

| | |
|---|---|
| Generation: | Parent to F1 |
| Seed Planted: | 46A05 (Breeder code = NS0705, a Pioneer Hi-Bred spring canola variety, commercially available from Proven Seed) and CYCLONE ™ (spring canola variety, commercially available from King Agro). |
| Seed Harvested: | 94SN-0680 = (46A05 × CYCLONE ™) |
| Method: | Parents were grown, and the crossing was carried out in a controlled environment in the greenhouse. |
| Generation: | Single cross F1 to three-way cross F1 |
| Seed Planted: | 94SN-0680 and NS0541 (Non registered, non-commercial Pioneer Hi-Bred spring canola line, homozygous for the IMI resistant genes) |
| Seed Harvested: | 94SN-5467 = (NS0541 × (46A05 × CYCLONE ™)) |
| Method: | Parents were grown, and the crossing was carried out in a controlled environment in the greenhouse. NS0541 was used as a female parent. Approximately six female plants and more than 10 male plants were sampled in making the three-way cross. |
| Generation: | Three way cross F1 to doubled haploid (F-infinity) |
| Seed Planted: | 94SN-5467 = (NS0541 × (46A05 × CYCLONE ™)) |
| Seed Harvested: | 95DHS-2537 |
| Method: | Twelve plants of 94SN-5467 were planted in the growth room under controlled environment as donor plants. These plants were sprayed with the herbicide, PURSUIT ™ (imazethapyr), at 1x level. Immature buds were harvested from each donor plant and were crushed in a blender to produce a slurry [as described in Swanson, E. B. et al., "Efficient isolation of microspores and the production of microspore-derived embyros in *Brassica napus*", L. Plant Cell Reports, 6: 94–97, (1987); and Swanson, E. B., Microspore culture in Brassica, pp. 159–169 in Methods in Molecular Biology, vol. 6, Plant Cell and Tissue Culture, Humana Press, (1990)]. The slurry was then filtered through two layers of Nitex filters (48 µm pores) and collected in centrifuge tubes. The suspensions were centrifuged, decanted and washed three times for a total of 4 spins. Microspores were counted using a haemocytometer and plated in NLN medium [Lichter, R., "Induction of haploid plants from isolated pollen of *Brassica*_napus", Z. Pflanzenphysiol. Bd. 105: 427–434, (1982)], containing 40 µg/l PURSUIT ™, at a density of 60,000 microspores per ml. Ten ml of this suspension was poured into 100 × 25 mm petri plates, wrapped with parafilm, and placed in a Percival incubation chamber at 32.5° C. in darkness for 15 days. During this period, the microspores carrying the genes responsible for resistance to Imidazolinone herbicides were expected to survive and produce embryos. After 15 days, petri plates with cotyledonary embryos were put on a rotary shaker for 6 to 13 days before being transferred to solid 0.8% agar medium with 0.1% Gibberillic acid (GA) in petri plates. Transferred embryos were incubated in the dark at 4–8° C. for 7 to 10 days and removed to a Percival incubation chamber in light at 20 to 25° C. for 3 to 5 weeks. Selected embryos that regenerated were placed in soil in 72 cell flats or put back onto 0.8% agar with 0.1% GA for a further 3 to 5 weeks before they were transplanted to soil. Before flowering, plants were treated with 0.33% colchicine for 1.5 to 2.5 hours. Plant roots were washed free of soil prior to incubation in the colchicine solution. After treatment they were planted in 10 cm plastic pots. Upon flowering, plants with fertile (diploid) racemes were covered with perforated, clear plastic bags to produce selfed seeds. After flowering bags were removed and plants were dried down, seeds was harvested, cleaned, and catalogued with a DHS number. Lines with 100 seeds or more were prepared for nursery evaluation. |

-continued

| | |
|---|---|
| Generation: | Doubled haploid (DH) evaluation |
| Seed Planted: | 95DHS-2537 along with the check varieties 46A72 (NS1472) and 45A71 (NS1471). |
| Seed Harvested: | 20 grams of open pollinated seed from several random plants to carry out quality analysis. After completing the evaluation and finalizing the selections, the entire row of open pollinated seed was harvested for the selected lines including 95DHS-2537. |
| Method: | Several hundred IMI resistant spring canola doubled haploid lines, including 95DHS-2537, were planted in the breeding nursery (project X523A) for evaluation purpose. Each line was planted in a three-meter long row with approximately 100 seeds/row. Every 20th row (#1, 20, 40, 60 etc.) was planted with the imidazolinone resistant variety 46A72 as a quality check. Every 10th row (#10, 30, 50, etc.) was planted with the imidazolinone resistant variety 45A71 as a maturity and vigor check. The entire nursery was sprayed with PURSUIT ™ at 50 g/ha, when plants were at the 4-leaf stage. Another application of PURSUIT ™ at 50 g/ha was made when plants were at the rosette stage. Doubled haploid lines showing herbicide injury were noted. Observations were recorded on each row, including checks, for: days to flowering, days to maturity, agronomic score at flowering and agronomic score at maturity. At physiological maturity, lines to be harvested were selected visually. A twenty gram sample of open pollinated seed was harvested from each of the selected lines. The quality check rows of 46A72 were also harvested. The samples were analyzed in the lab for oil percentage, protein percentage, and total glucosinolates (micromoles/g of whole seed at 8.5% moisture) using NIR (Near Infrared Spectroscopy). The final selection was performed based on days to maturity, agronomic score at maturity, oil percentage, protein percentage and total glucosinolates. Several doubled haploid lines were selected, including 95DHS-2537. |
| Generation: | Greenhouse Pure seed increase |
| Seed Planted: | 95DHS-2537 |
| Seed Harvested: | 95DHS-2537 |
| Method: | Each selected line, including 95DH5-2537, was planted in the greenhouse using remnant seed. PURSUIT ™ was applied to all lines (200 g/ha) in order to confirm imidazolinone resistance. All lines were inoculated with blackleg (*Phoma lingam*) spores to induce the disease. Lines showing herbicide injury and/or susceptibility to blackleg were discarded. Selected lines were self-pollinated to produce approximately 20 g of pure seed. |
| Generation: | Field evaluation (R100 tests) |
| Seed Planted: | 95DHS-2537 |
| Seed Harvested: | 95DHS-2537 |
| Method: | The selected lines, including 95DHS-2537, were evaluated in an unreplicated yield trial (R103), planted at six locations in western Canada. The plot size was 9 square meters (6 m × 1.5 m). The seeding rate was 5.5 kg/ha. Appropriate check varieties were included in the trial. The same entries were also planted in a disease trial where blackleg inoculum was applied to ensure uniform disease infection. Observations recorded included: days to flowering, days to maturity, lodging score (1 = poor, 9 = good), yield, moisture percentage, oil percentage, protein percentage, and total glucosinolates. Parallel to yield testing, pure seed of each line was planted in a seed increase plot to produce seed for future yield trials. Statistical analysis was performed on data collected from yield sites. At the end of the season, 95DHS-2537 was selected for further advancement. |
| Generation: | Field evaluation (R300 tests) |
| Seed Planted: | NS2804 |
| Seed Harvested: | NS2804 |
| Method: | The selected lines from R100 trials were assigned new code numbers. 95DHS-2537 received the code, NS2804. NS2804 was evaluated in a four replicate trial planted at 14 locations. The trial was handled according to the protocol specified by the Western Canadian Canola/Rapeseed Recommending Committee (WCC/RRC - Procedures and Appendices). The plot size was 9 square meters (6 m × 1.5 m). Normal agronomic practices were followed. Observations recorded included: days to flowering, days to maturity, lodging score (1 = poor, 9 = excellent), blackleg score (1 = poor, 9 = excellent), plant height, and yield/ha. At harvest, a sample of seed of approximately 20 grams was collected, and used to determine oil percentage, protein percentage, total glucosinolates, fatty acid composition and green seed content. NS2804 was also evaluated in Herbicide Screening trials to confirm its tolerance to imidazolinone herbicides (PURSUIT ™ and ODYSSEY ™). This trial was planted at one location following the protocol specified by the WCC/RRC (WCC/RRC - Procedures and Appendices). The results were summarized, and selection was finalized. It was decided to advance NS2804 to R4 ("Co-op trials"). |
| Generation: | Field evaluation (Pioneer R400 trial & Co-op trials) |
| Seed Planted: | NS2804 |
| Seed Harvested: | NS2804 |
| Method: | NS2804 was evaluated in a replicated, multi-location trial (R400) conducted by Pioneer Hi-Bred. This four replicate trial was planted at 22 locations. The plot size was 9 square meters (6 m × 1.5 m). The WCC/RRC protocol (WCC/RRC Procedures and Appendices) was followed in these trials. Data collection from these trials was exactly the same as above. NS2804 was also entered in the Official Trials. These trials are conducted at more than 20 locations, coordinated by the Canola Co-op Coordinator of the Canola Council of Canada. These trials are all run to the WCC/RRC protocol. The data collected is similar to what has been described earlier. NS2804 was also evaluated in the 2nd year of Herbicide Screening trials to confirm its herbicide tolerance. The WCC/RRC procedure was followed for these trials. NS2804 was registered under the commercial name, 46A76. |

Table 1 illustrates the performance of canola variety 46A76 in comparison to the WCC/RRC check varieties during breeding trials. Table 2 compares the performance of canola variety 46A76 with canola varieties 46A65, 45A71, and 46A74.

TABLE 1

Comparison of *Brassica napus* Variety, 46A76, with WCC/RRC Check Varieties*

| Variety | Yield** (qu/ha) | Yield (% chks) | Maturity (days) | Oil (%) | Protein (%) | Blackleg (1–9) | Lodging (1–9) | Plant Height (cm) | 1000 Seed Weight (gm) | Green Seed (%) |
|---|---|---|---|---|---|---|---|---|---|---|
| 46A76 | 23.0 | 113.8 | 93.5 | 47.2 | 49.6 | 8.4 | 6.0 | 120.0 | 3.8 | 0.1 |
| Defender | 20.1 | 99.5 | 91.1 | 46.1 | 48.8 | 7.6 | 5.2 | 117.9 | 3.9 | 0.4 |
| Excel | 19.1 | 94.6 | 91.6 | 46.9 | 49.1 | 6.9 | 5.0 | 117.0 | 3.7 | 0.2 |
| Legacy | 21.3 | 105.4 | 91.1 | 46.6 | 49.5 | 6.5 | 5.6 | 113.2 | 3.9 | 0.2 |
| Checks Mean# | 20.2 | 99.8 | 91.3 | 46.5 | 49.1 | 7.0 | 5.3 | 116.0 | 3.8 | 0.3 |
| Difference† | 2.8 | 14.0 | 2.2 | 0.7 | 0.5 | 1.4 | 0.7 | 4.0 | -0.0 | -0.2 |

*Source of data: Pioneer Hi-Bred western Canadian canola trials and WCC/RRC co-op trials
**Trait Definitions: Yield = seed yield in quintals (decitonnes) per hectare, and as a percentage of Checks Mean; Maturity = days to physiological maturity; Oil & Protein as percentage of total seed weight at 8.5% moisture; Blackleg = disease score, where 9 = resistant and 1 = dead; Lodging = leaning of plant stand, where 9 = upright and 1 = prostrate; Plant Height = at end of flowering, in centimetres; 1000 Seed Weight = weight in grams of 1000 mature seeds; Green Seed = percentage of mature seed which is green inside when crushed.
Checks = Defender, Excel, and Legacy (WCC/RRC registration check varieties during period of testing)
†Difference = Difference between canola variety 46A76 and Checks Mean

TABLE 2

Comparison of *Brassica napus* Variety 46A76 with canola Varieties 46A65, 45A71 and 46A74*

| Variety | Yield** (qu/ha) | Yield (% chks) | Maturity (days) | Oil (%) | Protein (%) | Blackleg (1–9) | Lodging (1–9) | Plant Height (cm) | 1000 Seed Weight (gm) | Green Seed (%) |
|---|---|---|---|---|---|---|---|---|---|---|
| 46A76 | 22.4 | 103.7 | 91.8 | 47.5 | 49.9 | 8.4 | 6.7 | 126.9 | 3.8 | 0.2 |
| 46A65 | 21.6 | 100.0 | 90.1 | 47.8 | 50.7 | 8.3 | 7.1 | 119.3 | 3.4 | 0.1 |
| Difference† | 0.8 | 3.7 | 1.7 | -0.3 | -0.8 | 0.1 | -0.4 | 7.6 | 0.4 | 0.1 |
| LOCS | 26 | 26 | 22 | 26 | 26 | 3 | 10 | 21 | 14 | 23 |
| 46A76 | 22.4 | 109.3 | 91.8 | 47.5 | 49.9 | 8.4 | 6.7 | 126.9 | 3.8 | 0.2 |
| 45A71 | 20.5 | 100.0 | 89.5 | 46.5 | 48.1 | 6.4 | 5.8 | 126.0 | 4.1 | 0.2 |
| Difference† | 1.9 | 9.3 | 2.3 | 1.0 | 1.8 | 2.0 | 0.9 | 0.9 | -0.3 | 0.0 |
| LOCS | 26 | 26 | 22 | 26 | 26 | 3 | 10 | 21 | 14 | 23 |
| 46A76 | 19.0 | 109.8 | 92.5 | 46.6 | 47.4 | 8.5 | 6.3 | 129.4 | | 0.2 |
| 46A74 | 17.3 | 100.0 | 93.8 | 45.6 | 49.2 | 8.2 | 6.1 | 123.8 | | 0.7 |
| Difference† | 1.7 | 9.8 | -1.3 | 1.0 | -1.8 | 0.3 | 0.2 | 5.6 | 0.0 | -0.5 |
| LOCS | 12 | 12 | 8 | 12 | 12 | 1 | 3 | 7 | | 9 |

*Data Source: Pioneer Hi-Bred private trials
**Trait Definitions: Yield = seed yield in quintals (decitonnes) per hectare, and as a percentage of Checks Mean; Maturity = days to physiological maturity; Oil & Protein as percentage of total seed weight at 8.5% moisture; Blackleg = disease score, where 9 = resistant and 1 = dead; Lodging = leaning of plant stand, where 9 = upright and 1 = prostrate; Plant Height = at end of flowering, in centimeters; 1000 Seed Weight = weight in grams of 1000 mature seeds; Green Seed = percentage of mature seed which is green inside when crushed.
†Difference = Difference between canola variety 46A76 and comparison variety.
LOCS = Number of locations at which varieties were tested

Example 2

Development of the Improved IMI Resistant *Brassica napus* Line, NS3213.

| | |
|---|---|
| Generation: | Parent to F1 |
| Seed Planted: | LEGACY ™ (Registered variety from Svalof-Weibulls), and 46A05 (Breeder code = NS0705, a Pioneer Hi-Bred spring canola line, commercially available from Proven Seed) |
| Seed Harvested: | 94SN-0658 = (LEGACY ™ × 46A05) |
| Method: | Parents were grown, and the crossing was carried out in a controlled environment in the greenhouse. |
| Generation: | Single cross F1 to three-way cross F1 |
| Seed Planted: | 94SN-0658 = (LEGACY ™ × 46A05) and 45A71 (Breeder Code NS1471, registered imidazolinone resistant spring canola variety from Pioneer Hi-Bred, commercially available from Proven Seed). |
| Seed Harvested: | 96-SN-0510 = (45A71 × (LEGACY ™ × 46A05)) |
| Method: | Parents were grown, and the crossing was carried out in a controlled environment in the greenhouse. 45A71 was used as a female parent. Approximately six female plants and more than 10 male plants were sampled in making the three-way cross. Imidazolinone resistance was contributed by 45A71, which is homozygous for the two IMI resistance genes. |
| Generation: | Three-way cross F1 to doubled haploid (F-infinity) |
| Seed Planted: | 96-SN-0510 = (45A71 × (LEGACY ™ × 46A05)) |
| Seed Harvested: | 97DHS-2044 |
| Method: | Twelve plants of 96SN-0510 were planted in the growth room under controlled environment as donor plants. These plants were sprayed with the herbicide, PURSUIT ™ (imazethapyr), at 1x level. Immature buds were harvested from each donor plant and were crushed in a blender to produce a slurry [as described in Swanson, E. B. et al., "Efficient isolation of microspores and the production of microspore-derived embyros in *Brassica napus*", L. Plant Cell Reports, 6: 94–97, (1987); and Swanson, E.B., Microspore culture in Brassica, pp. 159–169 in Methods in Molecular Biology, vol. 6, Plant Cell and Tissue Culture, Humana Press, (1990)]. The slurry was then filtered through two |

-continued

|  |  |
|---|---|
| | layers of Nitex filters (48 μm pores) and collected in centrifuge tubes. The suspensions were centrifuged, decanted and washed three times for a total of 4 spins. Microspores were counted using a haemocytometer and plated in NLN medium (Lichter, R. "Induction of haploid plants from isolated pollen of Brassica napus", Z. Pflanzenphysiol. Bd. 105: 427–434, (1982)), containing 40 μg/l PURSUIT ™, at a density of 60,000 microspores per ml. Ten ml of this suspension was poured into 100 × 25 mm petri plates, wrapped with parafilm, and placed in a Percival incubation chamber at 32.5° C. in darkness for 15 days. During this period, the microspores carrying the genes responsible for resistance to Imidazolinone herbicides were expected to survive and produce embryos. After 15 days, petri plates with cotyledonary embryos were put on a rotary shaker for 6 to 13 days before being transferred to solid 0.8% agar medium with 0.1% Gibberillic acid (GA) in petri plates. Transferred embryos were incubated in the dark at 4–8° C. for 7 to 10 days and removed to a Percival incubation chamber in light at 20 to 25° C. for 3 to 5 weeks. Selected embryos that regenerated were placed in soil in 72 cell flats or put back onto 0.8% agar with 0.1% GA for a further 3 to 5 weeks before they were transplanted to soil. Before flowering, plants were treated with 0.33% colchicine for 1.5 to 2.5 hours. Plant roots were washed free of soil prior to incubation in the colchicine solution. After treatment they were planted in 10 cm plastic pots. Upon flowering, plants with fertile (diploid) racemes were covered with perforated, clear plastic bags to produce selfed seeds. After flowering bags were removed and plants were dried down, seeds was harvested, cleaned, and catalogued with a DHS number. Lines with 100 seeds or more were prepared for nursery evaluation. |
| Generation: | Doubled haploid evaluation |
| Seed Planted: | 97DHS-2044 along with the check varieties 46A72 (NS1472) and 45A71 (NS1471). |
| Seed Harvested: | In order to perform quality analysis, twenty grams of open pollinated seed was harvested from several random plants of 97DHS-2044. Also, the same amount of open pollinated seed was harvested from the selected check rows. After completing the evaluation and finalizing the selections, an entire row of open pollinated seed was harvested for the selected lines (including 97DHS-2044). |
| Method: | Several hundred imidazolinone resistant spring canola doubled haploid lines, including 97DHS-2044, were planted in the breeding nursery (project X723A) for evaluation purposes. Each line was planted in a three-meter long row with approximately 100 seeds/row. Every 20th row (#1, 20, 40, etc.) was planted to the imidazolinone resistant variety 46A72 as a quality check. Every 10th row (#10, 30, 50, etc.) was planted with the imidazolinone resistant variety 45A71 as a maturity and vigor check. The entire nursery was sprayed with PURSUIT ™ at 50 g/ha when plants were at the 4-leaf stage. Another application of PURSUIT ™ at 50 g/ha was made when plants were at the rosette stage. Doubled haploid lines showing herbicide injury were noted. Observations were recorded on each row, including checks, for: days to flowering, days to maturity, agronomic score at flowering and agronomic score at maturity. At physiological maturity, lines to be harvested were selected visually. A sample of twenty grams of open pollinated seed was harvested from each of the selected lines. The quality check rows of 46A72 were also harvested. The samples were analyzed in the lab for oil percentage, protein percentage, and total glucosinolates (micromoles/gram of whole seed at 8.5% moisture) using NIR (Near Infrared Spectroscopy). The final selection was performed based on days to maturity, agronomic score at maturity, oil percentage, protein percentage and total glucosinolates. Several doubled haploid lines were selected including 97DHS-2044. |

-continued

|  |  |
|---|---|
| Generation: | Greenhouse Pure seed increase |
| Seed Planted: | 97DHS-2044 |
| Seed Harvested: | 97DHS-2044 |
| Method: | Each selected line, including 97DH5-2044, was planted in the greenhouse (GH project SN-615) using remnant seed. PURSUIT ™ was applied to all lines (200 g/ha) in order to confirm imidazolinone resistance. All lines were inoculated with blackleg (*Phoma lingam*) spores to induce disease. Lines showing herbicide injury and/or susceptibility to blackleg were discarded. Selected lines were self-pollinated to produce approximately 20 g of pure seed, and were assigned new code numbers. 97SN-2044 was assigned the code NS3213. |
| Generation: | Field evaluation (R200 tests) |
| Seed Planted: | NS3213 |
| Seed Harvested: | NS3213 |
| Method: | The selected lines, including NS3213, were evaluated in a two replicate yield trial (R204) planted at six locations in western Canada. Plot size was 9 square meters (6 m × 1.5 m). The seeding rate was 5.5 kg/ha. Appropriate check varieties were also included in the trial. The same entries were also planted in a disease trial where blackleg inoculum was applied to ensure uniform disease infection. Observations recorded included: days to flowering, days to maturity, lodging score (1 = poor, 9 = good), yield (q/ha), and moisture percentage. At harvest, a 20 g seed sample was collected from each plot, and analyzed to determine: oil percentage, protein percentage, total glucosinolates, and fatty acid composition. Pure seed of each line was planted in a seed increase plot in order to produce seed for future testing. Statistical analysis was performed on data collected from different sites. At the end of the season, NS3213 was selected for further advancement. |
| Generation: | Field evaluation (R300 tests) |
| Seed Planted: | NS3213 |
| Seed Harvested: | NS3213 |
| Method: | The selected lines, including NS3213, were evaluated in a four replicate trial planted at 16 locations. The trial was handled according to the protocol specified by the Western Canadian Canola/Rapeseed Recommending Committee (WCC/RRC - Procedures and Appendices). The plot size was 9 square meters (6 m × 1.5 m). Normal agronomic practices were followed. Observations recorded included: days to flowering, days to maturity, lodging score (1 = poor, 9 = excellent), blackleg score (1 = poor, 9 = excellent), plant height, and yield/ha. At harvest, a sample of seed of approximately 20 grams was collected, and used to determine oil percentage, protein percentage, total glucosinolates, fatty acid composition and green seed content. NS3213 was also evaluated in Herbicide Screening trials to confirm its tolerance to imidazolinone herbicides (PURSUIT ™ and ODYSSEY ™). This trial was planted at one location following the protocol specified by the WCC/RRC (WCC/RRC - Procedures and Appendices). The results were summarized, and selection was finalized. It was decided to advance NS3213 to R4 (Co-op trials). |
| Generation: | Field evaluation (R400 tests - or Co-op trials) |
| Seed Planted: | NS3213 |
| Seed Harvested: | NS3213 |
| Method: | NS3213 is being evaluated in four replicate, multi-location trials (R400) conducted by Pioneer Hi-Bred. This trial is planted at 22 locations. The plot size is 9 square meters (6 m × 1.5 m). These trials are being conducted according to the WCC/RRC protocol (WCC/RRC Procedures and Appendices). Data collection from these trials is exactly the same as above. |

Table 3 illustrates the performance of *Brassica napus* variety, NS3213, in comparison to WCC/RRC check varieties during experimental trials. Table 4 provides a comparison of *Brassica napus* variety, NS3213, with varieties 46A65, 45A71, and 46A76.

TABLE 3

Comparison of *Brassica napus* Variety, NS3213, with WCC/RRC Check Varieties*

| Variety | Yield** (qu/ha) | Yield (% chks) | Maturity (days) | Oil (%) | Protein (%) | Blackleg (1–9) | Lodging (1–9) | Plant Height (cm) | Total Glucs. (uM/g) | 1000 Seed Weight (g) | Green Seed (%) |
|---|---|---|---|---|---|---|---|---|---|---|---|
| NS3213 | 29.9 | 120.6 | 98.8 | 48.3 | 47.2 | 7.9 | 5.8 | 119.6 | 13.0 | 3.5 | 0.7 |
| Defender | 26.2 | 105.6 | 97.7 | 47.1 | 47.3 | 7.3 | 5.8 | 121.2 | 13.8 | 3.4 | 0.7 |
| Excel | 23.1 | 93.1 | 98.8 | 47.3 | 46.8 | 5.7 | 5.6 | 123.2 | 16.8 | 3.2 | 1.1 |
| Legacy | 25.1 | 101.2 | 98.3 | 47.1 | 47.8 | 4.9 | 5.5 | 118.0 | 11.5 | 3.2 | 1.0 |
| Check Mean# | 24.8 | 100.0 | 98.3 | 47.2 | 47.3 | 6.0 | 5.6 | 120.8 | 14.0 | 3.3 | 0.9 |
| Difference† | 5.1 | 20.6 | 0.5 | 1.1 | −0.1 | 1.9 | 0.2 | −1.2 | −1.0 | 0.2 | −0.2 |

*Source of data: Pioneer Hi-Bred western Canadian private canola trials
**Trait Definitions: Yield = seed yield in quintals (decitonnes) per hectare, and as percentage of Checks Mean; Maturity = days to physiological maturity; Oil & Protein as percentage of total seed weight at 8.5% moisture; Blackleg = disease score, where 9 is best and 1 is worst; Lodging = leaning of plant stand, where 9 = upright and 1 = prostrate; Plant Height = at end of flowering, in centimetres; Glucosinolates = total aliphatic glucosinolates. in seed at 8.5% moisture, expressed in micromoles per gram; 1000 Seed Weight = weight in grams of 1000 mature seeds; Green Seed = percent of mature seed which is green inside when crushed.
Checks = Defender, Excel, and Legacy, (WCC/RRC registration checks during period of testing)
†Difference = Difference between 46A76 and Check Mean

TABLE 4

Comparison of *Brassica napus* Variety NS3213 with Canola Varieties 46A65, 45A71, and 46A76.*

| Variety | Yield** (qu/ha) | Yield (% chks) | Maturity (days) | Oil (%) | Protein (%) | Blackleg (1–9) | Lodging (1–9) | Plant Height (cm) | Gluco-sinolates (uM/g) | 1000 Seed Weight (gm) | Green Seed (%) |
|---|---|---|---|---|---|---|---|---|---|---|---|
| NS3213 | 29.9 | 108.7 | 98.9 | 48.3 | 47.2 | 7.9 | 5.8 | 119.6 | 13 | 3.5 | 0.7 |
| 46A65 | 27.5 | 100.0 | 99.8 | 48.5 | 48.3 | 8.4 | 6.5 | 118.7 | 14.5 | 3.1 | 0.3 |
| Difference | 2.4 | 8.7 | −0.9 | −0.2 | −1.1 | −0.5 | −0.7 | 0.9 | −1.5 | 0.4 | 0.4 |
| LOCS | 19.0 | | 15.0 | 19.0 | 19.0 | 3.0 | 9.0 | 11.0 | 19.0 | 12.0 | 11.0 |
| NS3213 | 22.2 | 105.2 | 97.8 | 44.7 | 48.1 | 8.5 | 5.7 | 116.7 | 12.2 | | |
| 45A71 | 21.1 | 100.0 | 99.8 | 44.9 | 47.7 | 7.8 | 5.8 | 120.0 | 10.7 | | |
| Difference | 1.1 | 5.2 | −2.0 | −0.2 | 0.4 | 0.7 | −0.1 | −3.3 | 1.5 | 0.0 | 0.0 |
| LOCS | 4.0 | | 2.0 | 4.0 | 4.0 | 1.0 | 3.0 | 3.0 | 4.0 | | |
| NS3213 | 32.0 | 107.0 | 99.0 | 49.2 | 47.0 | 7.7 | 5.8 | 120.7 | 13.2 | 3.5 | 0.7 |
| 46A76 | 29.9 | 100.0 | 100.1 | 48.2 | 47.0 | 8.1 | 7.1 | 126.5 | 12.1 | 3.3 | 0.4 |
| Difference | 2.1 | 7.0 | −1.1 | 1.0 | 0.0 | −0.4 | −1.3 | −5.8 | 1.1 | 0.2 | 0.3 |
| LOCS | 15.0 | | 13.0 | 15.0 | 15.0 | 2.0 | 6.0 | 8.0 | 15.0 | 12.0 | 11.0 |

*Data Source: Pioneer Hi-Bred western Canadian private canola trials
**Trait Definitions: Yield = seed yield in quintals (decitonnes) per hectare, and as percentage of Checks Mean; Maturity = days to physiological maturity; Oil & Protein as percentage of total seed weight at 8.5% moisture; Blackleg = disease score, where 9 = resistant and 1 = highly susceptible; Lodging = leaning of plant stand, where 9 = upright and 1 = prostrate; Plant Height = at end of flowering, in centimetres; Glucosinolates = total aliphatic glucosinolates in seed at 8.5% moisture, expressed in micromoles per gram; 1000 Seed Weight = weight in grams of 1000 mature seeds; Green Seed = percentage of mature seed which is green inside when crushed.
LOCS = Number of locations at which varieties were tested.
†Difference = Difference between canola variety NS3213 and comparison variety

Deposits

This invention is not to be construed as limited to the particular embodiments disclosed, since these are regarded as illustrative rather than restrictive. Moreover, variations and changes may be made by those skilled in the art without departing from the spirit of invention.

The seeds of the subject invention were deposited in the American Type Culture Collection (ATCC), 10801 University Blvd., Manassas, Va. 20110-2209, USA:

| Seed | Accession Number | Deposit Date |
|---|---|---|
| *Brassica napus* 46A76 | PTA-2469 | September 14, 2000 |
| *Brassica napus* NS3213 | PTA-2471 | September 14, 2000 |

What is claimed is:

1. A plant cell of a *Brassica napus* plant having an "R" rating blackleg and resistance to at least one AHAS-inhibltor herbicide, wherein said plant is designated variety NS3213, representative seed of said variety having been deposited under ATCC Accession No. PTA-2471.

2. A tissue culture of regenerable cells of a *Brassica* plant having an "R" rating for blackleg and resistance to at least one AHAS-inhibitor herbicide, wherein said plant is designated variety NS3213, representative seed of said variety having been deposited under ATCC Accession No. PTA-2471.

3. A *Bressica* plant having an "R" rating for blackleg and resistance to at least one AHAS-inhibitor herbicide produced from the tissue culture of claim 2.

4. A *Brassica* plant or plant part having an "R" rating for blackleg and resistance to at least one AHAS-inhibitor herbicide, wherein said plant is designated variety NS3213, representative seed of said variety having been deposited under ATCC Accession No. PTA-2471.

5. The plant part in accordance with claim 4, wherein said plant part is selected from the group consisting of tissue, pollen, ovules, roots, leaves, cotyledons, hypocotyls, embryos, pods, flowers, shoots, stalks, seeds, and rnicrospores.

6. A method for regenerating a *Brassice* plant having an "R" rating for blackleg and resistance to at least one AHAS-inhibitor herbicide, the method comprising growing the plant part of claim 4 under conditions sufficient to regenerate a *Brassice* plant.

7. A method of breeding a *Brassica* line comprising crossing a first *Brassica* plant having an "R" rating for blackleg and resistance to at least one AHAS-inhibitor herbicide with a second *Brasslca* plant to produce an F1 progeny plant, wherein said first *Brassica* plant is designated variety NS3213, representative seed of said variety having been deposited under ATCC Accession No. PTA-2471.

8. The method according to claim 7, wherein said F1 progeny plant is further used in a breeding program selected from the group consisting of pedigree breeding, self-pollination, haploidy, single seed descent, modified single seed descent and backcrossing followed by selecting for a *Brassica* line that has an "R" rating for blackleg and resistance to at least one AHAS-inhibitor herbicide.

9. The method according to claim 7, wherein said second plant is *Brassica napus*.

10. The method according to claim 7, wherein said second plant is *Brassica juncea*.

11. The method according to claim 7, wherein said second plant is *Brassica rapa*.

12. A method for producing a first generation (F1) hybrid *Brassica* seed comprising crossing a first *Brassica* plant having resistance to at least one AHAS-inhibitor herbicide and an "R" rating for blackleg with a second *Brassica* plant different than said first *Brassica* plant and harvesting the resultant first generation (F1) hybrid *Brassica* seed, wherein said first *Brassica* plant is designated variety NS3213, representative seed of said variety having been deposited under ATCC Accession No. PTA-2471.

13. The method in accordance with claim 12, wherein said second *Brassica* plant is *Brassica napus*.

14. The method in accordance with claim 12, wherein said second *Brassica* plant is *Brassica juncea*.

15. The method in accordance with claim 12, wherein said second *Brassica* plant is *Brassica rapa*.

16. A *Brassica napus* F1 progeny plant or plant part of variety NS3213, wherein said progeny plant or plant part has an "R" rating for blackleg and resistance to at least one AHAS-inhibitor herbicide, representative seed of said variety having been deposited under ATCC Accession No. PTA-2471.

17. A *Brassica napus* F1 progeny plant seed of variety NS3213, wherein said progeny plant seed has an "R" rating for blackleg and resistance to at least one AHAS-inhibitor herbicide, representative seed of said variety having been deposited under ATCC Accession No. PTA-2471.

18. A *Brassica napus* F1 progeny plant cell of variety NS3213, wherein said progeny plant cell has an "R" rating for blackleg and resistance to at least one AHAS-inhibitor herbicide, representative seed of said variety having been deposited under ATCC Accession No. PTA-2471.

* * * * *